United States Patent
Suh et al.

(10) Patent No.: US 9,557,272 B2
(45) Date of Patent: Jan. 31, 2017

(54) SUBSTRATE FOR SURFACE-ENHANCED RAMAN SPECTROSCOPY AND METHOD FOR PRODUCING SAME

(71) Applicants: Korea Institute of Machinery & Materials, Yuseong-Gu, Daejeon (KR); Korea Research Institute of Chemical Technology, Yuseong-Gu, Daejeon (KR)

(72) Inventors: Yung Doug Suh, Daejeon (KR); Jung Heum Yun, Gimhae (KR); Sung Gyu Park, Changwon-si (KR); Hae Mi Lee, Daejeon (KR); Gun Hwan Lee, Pyeongtaek (KR); Dong Ho Kim, Changwon-si (KR)

(73) Assignees: Korea Institute of Machinery & Materials, Yuseong-Gu, Daejeon (KR); Korea Research Institute of Chemical Technology, Yuseong-Gu, Daejeon (KR)

( * ) Notice: Subject to any disclaimer, the term of this patent is extended or adjusted under 35 U.S.C. 154(b) by 0 days.

(21) Appl. No.: 15/021,415

(22) PCT Filed: Sep. 16, 2014

(86) PCT No.: PCT/KR2014/008613
§ 371 (c)(1),
(2) Date: Mar. 11, 2016

(87) PCT Pub. No.: WO2015/041442
PCT Pub. Date: Mar. 26, 2015

(65) Prior Publication Data
US 2016/0223467 A1 Aug. 4, 2016

(30) Foreign Application Priority Data
Sep. 17, 2013 (KR) .......... 10-2013-0112087

(51) Int. Cl.
*G01J 3/44* (2006.01)
*G01N 21/65* (2006.01)
(Continued)

(52) U.S. Cl.
CPC .......... *G01N 21/658* (2013.01); *C09D 7/1216* (2013.01); *C23C 16/44* (2013.01);
(Continued)

(58) Field of Classification Search
CPC  G01N 21/65; G01N 21/658; G01N 2021/656; G01J 3/44; G01J 3/02; C23C 16/44; G09D 7/12
See application file for complete search history.

(56) References Cited

U.S. PATENT DOCUMENTS 8,257,678 B2 * 9/2012 Steiner, III ............ B82Y 30/00
423/447.1

FOREIGN PATENT DOCUMENTS

KR          10-1097205 B1    12/2011
KR    10-2012-0000219 A      1/2012
(Continued)

OTHER PUBLICATIONS

International Search Report mailed Dec. 31, 2014 in connection with PCT/KR2014/008613.

*Primary Examiner* — Abdullahi Nur
(74) *Attorney, Agent, or Firm* — Wolf, Greenfield & Sacks, P.C.

(57) ABSTRACT

Disclosed are a substrate for surface-enhanced Raman spectroscopy allowing surface-enhanced Raman signals to be notably improved, even in cases of long-term storage, by producing the substrate so that metal nanoparticles thereon are distanced several nanometers apart, and a method for
(Continued)

producing the substrate for surface-enhanced Raman spectroscopy at a large scale with simple equipment and at a low production cost.

20 Claims, 4 Drawing Sheets

(51) Int. Cl.
    *C09D 7/12*     (2006.01)
    *C23C 16/44*     (2006.01)
    *B82Y 15/00*     (2011.01)

(52) U.S. Cl.
    CPC ........ *B82Y 15/00* (2013.01); *G01N 2201/068* (2013.01); *G01N 2201/06113* (2013.01); *Y10S 977/954* (2013.01)

(56) References Cited

FOREIGN PATENT DOCUMENTS

| | | |
|---|---|---|
| KR | 10-2013-0003843 A | 1/2013 |
| KR | 10-1272316 B1 | 6/2013 |
| WO | WO 2010/056258 A1 | 5/2010 |

\* cited by examiner

SUBSTRATE FOR SURFACE-ENHANCED RAMAN SPECTROSCOPY AND METHOD FOR PRODUCING SAME

CROSS REFERENCE TO RELATED APPLICATION(S)

This application is the national phase application pursuant to 35 U.S.C. §371 of International Application No. PCT/KR2014/008613, filed Sep. 16, 2014, which claims the benefit under 35 USC §119(a) of Korean Patent Application No. 10-2013-0112087 filed on Sep. 17, 2013 in the Korean Intellectual Property Office, the entire disclosures of which are incorporated herein by reference for all purposes.

BACKGROUND

1. Field

The following description relates to a substrate for surface-enhanced Raman spectroscopy allowing Surface-enhanced Raman spectroscopic signals to be notably improved, even in cases of long-term storage, by producing the substrate so that metal nanoparticles thereon are distanced several nanometers apart, and to a method for producing a substrate for surface-enhanced Raman spectroscopy at a large scale with simple equipment and at a low production cost.

2. Description of Related Art

Raman scattering or the Raman Effect is an inelastic photon scattering phenomenon. When photons are scattered from an atom or molecule, most photons are elastically scattered (Rayleigh scattering), such that the scattered photons have the same energy (frequency and wavelength) as the incident photons. A small fraction of the scattered photons (approximately 1 in 10 million) are scattered by an excitation, with the scattered photons having a frequency different from, and usually lower than, that of the incident photons. In a gas, Raman scattering can occur with a change in energy of a molecule due to a transition to another (usually higher) energy level.

Raman Effect (Raman shift) is exhibited in almost organic molecules including not only by polar molecules but also by non-polar molecules which have induction polarizability when Raman spectroscopy using Raman scattering is applied. It is thus more suitable for the detection of biomolecules such as proteins, genes and the like since it is not affected by interference caused by water molecules.

On the other hand, specific wavelengths of Raman emission spectrum represents chemical composition and structure features so that it can be used to directly analyze materials using Raman signals.

Even though an analyte can be analyzed directly, it has not been practically used, except to academic researches, because it requires costly equipments to detect very week signals and has very low reproducibility of signals. In order to overcome such drawbacks, in 1974, Fleischmann et al. reported enhancements of Raman signals of pyridine adsorbed on a silver electrode roughened by successive oxidation-reduction cycles. The signals were $10^6$ higher than expected, and they were originally explained as being due to the additional surface area provided by the roughening of the surface. That is, the surface-enhanced Raman spectroscopy is a phenomenon showing enhancements of Raman signals of a targeted molecule when the molecule is present around the metallic nanostructure.

Analysis using the surface-enhanced Raman scattering provides information which can be difficult to obtain through a typical Raman analysis. It is needed to study how a material to be analyzed interacts with a surface in order to determine whether a surface-enhanced Raman scattering analysis is possible. Since various surface interactions are involved between a material to be analyzed and the surface of a metal, enhanced Raman signals, which cannot be provided by a typical Raman analysis, are adsorbed. The surface-enhanced Raman scattering may occur when a material to be analyzed is adsorbed or close to a metallic surface. Coherent free electron oscillations that exist at the interface between a metal and incident light must occur to efficiently enhance Raman emission. This is called as a surface plasmon which provides electromagnetic enhancement. The incident light creates surface plasmons (electromagnetic effect) on a metal surface which enhance Raman emission through interaction (charge-transfer effect) with an analyte.

Roughness of the surface of a substrate on which an analyte is placed roles an important factor for occurrence of surface plasmons and enormous enhancement of Raman signals therefrom. Thus, various studies using nanotechnologies have been developed to roughen the surface of a substrate to provide nanostructures such as nanometer-sized columns, linear broken surface or nanoparticles.

Generally, optical, electrical, physical and chemical properties of a metallic nano material can be controlled by changing its size, shape, crystalline structure and the like. Precious metal nanoparticles composed of Au or Ag strongly resonate with light in the visible region to yield strong absorption and scattering.

A surface plasmon resonance frequency varies with various factors, for example, such as kind, for example, such as Au, Ag, Cu, Pt, Pd and the like, size, and shape of metal nanoparticles, a solvent into which metal nanoparticles are dispersed, a kind of laser (incident light) and the like. Thus, surface-enhanced Raman signals can be obtained by controlling these factors.

Surface-enhanced Raman scattering is a technique to analyze a trace amount of a material by enhancing Raman signals through surface Plasmon resonance on a metal surface including nanometer-sized structures, for example, such as metal particles or patterns. Reproducibility of signals should be resolved to commercialize the surface-enhanced Raman scattering technique. Producing Raman probes should be also resolved through structural control of nanoparticles or patterns to commercialize the surface-enhanced Raman scattering technique. However, there is still limit to reproducibly produce enhanced Raman signals at a large scale. One approach to resolve those problems is patterning a substrate for surface-enhanced Raman spectroscopy in a large scale. This approach includes a top-down method, for example, such as an e-beam lithography and a focused ion beam milling, and a bottom-up method, for example, such as patterning using a mold and a colloidal lithography.

The bottom-up method allows massive parallel processing and rapid production of patterned nanostructures economically at a large scale. On the other hand, the top-down method allows excellent control of size and shape of particles, but requires high production cost and has limitation in implementing at a large scale.

However, since the surface-enhanced Raman scattering technology can detect even with a trace amount of an analyte at a low intensity, much attention has been given to their study in a biosensor application field. The surface-enhanced Raman scattering technology can provide information on the chemical structure of an analyte in a narrow spectrum and allow multiple detections since each molecule has its own unique Raman signal unlike existing fluorescence analysis. Thus, a great deal of development research is currently under way on detections of bio materials (DNAs, proteins, cells, etc.) and disease diagnosis devices utilizing the surface-enhanced Raman scattering technology. In addition, surface-enhanced Raman diagnosis devices having continuous reproducibility can be implemented using microfluidic devices and Raman spectroscopic technique.

Accordingly, inventors of this following description have found a substrate for surface-enhanced Raman spectroscopy which allows surface-enhanced Raman signals to be notably improved, even in cases of long-term storage, by producing the substrate so that metal nanoparticles thereon are distanced several nanometers apart, and a method for producing the substrate for surface-enhanced Raman spectroscopy at a large scale with simple equipment and at a low production cost. Inventors have also found a method for producing a substrate for surface-enhanced Raman spectroscopy which includes forming uniform protuberant structures having protruded curved surface on a polymer substrate using plasma dry etching, and depositing a metal using vapor deposition to provide a substrate for surface-enhanced Raman spectroscopy having metal nanoparticles distanced several nanometers apart on the metal.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

According to one general aspect, a substrate for surface-enhanced Raman spectroscopy includes metal nanoparticles which are uniformly spaced several nanometers apart with each other on the surface in a large scale, allows surface-enhanced Raman signals to be notably improved, even in cases of long-term storage, and allows quantitative analysis due to reproducible enhancement effects.

According to another general aspect, a method for producing a substrate for surface-enhanced Raman spectroscopy produces at a large scale with simple equipment and at a low production cost and reproducibly produces the distance between the metal nanoparticles to be several nanometers.

According to another general aspect, a Raman spectroscopic device includes a light source; the substrate for surface-enhanced Raman spectroscopy described above; and a detector configured to detect Raman spectrum.

According to another general aspect, a method for detecting Raman spectroscopy of an analyte includes: preparing the substrate for surface-enhanced Raman spectroscopy described above; approaching or contacting an analyte to the substrate; irradiating the analyte; and detecting scattered Raman signals of the analyte.

A substrate for surface-enhanced Raman spectroscopy according to an example may include a polymer substrate of which protuberant structures having an upper protruded curved surface are formed to be spaced-apart on a first surface; metal-containing nanoparticles formed on the protuberant structures; and a metal-containing thin layer formed on a part or the entire part of the first surface of the polymer substrate where the protuberant structures are not formed, wherein the metal-containing nanoparticle forms a nanogap with an adjacent metal-containing nanoparticle, an adjacent metal-containing thin layer or both to create a surface plasmon resonance during irradiating a light.

A Raman spectroscopic device may include a light source; the substrate for surface-enhanced Raman spectroscopy described above; and a detector configured to detect Raman spectrum. The light source may a laser which can provide a high energy incident light.

A method for detecting Raman spectroscopy of an analyte may include: preparing a substrate for surface-enhanced Raman spectroscopy; approaching or contacting an analyte to the substrate; irradiating the analyte; and detecting scattered Raman signals of the analyte.

DETAILED DESCRIPTION

Figure 1:
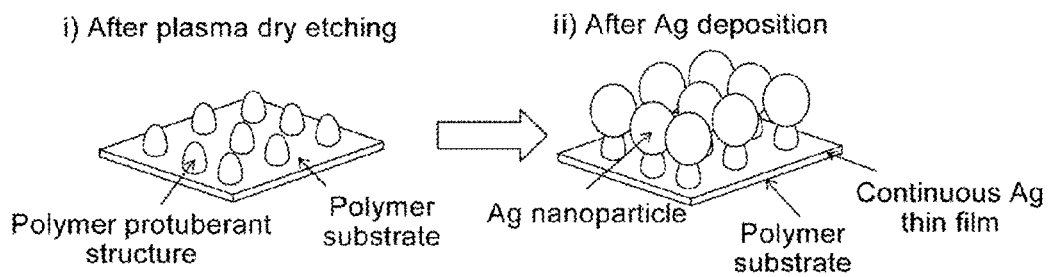
FIG. 1 is diagrams illustrating an example of a substrate for surface-enhanced Raman spectroscopy and an example of a method for manufacturing the same.
Figure 2:
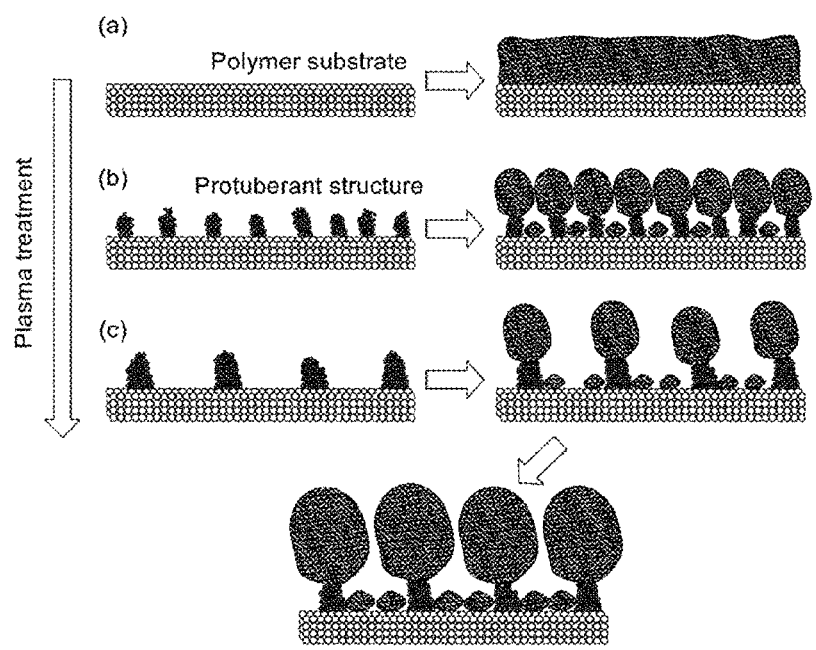
FIG. 2 is diagrams illustrating examples of structures formed by a metal deposition depending on a presence and a distance of protuberant structures on a polymer substrate.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

Throughout the description of the present disclosure, a term "surface-enhanced Raman spectroscopy (SERS)" may be also called as surface-enhanced Raman scattering. The surface-enhanced Raman spectroscopy determines Raman scattering signal enhanced of a material to be analyzed which is adsorbed on or present within a distance of several hundred nanometers from a roughen surface of a Raman active material, for example, such as a metal. The intensity of enhanced signal can be higher $10^4$ to $10^6$ than that of conventional Raman signal, as being due to a surface plasmon provided by the roughening of the surface.

General Raman scattering, which is an inelastic photon scattering phenomenon, can occur with a change in energy of a molecule due to a vibrational transition to another energy level when light encounters the molecule. Unlike infrared spectroscopy which measures vibrational energy to cause a change in dipole moment and is thus widely used to analyze the vibrational transition, the Raman spectroscopy can detect signals of a nonpolar molecule having a change in induced polarizability and can be suitable for detecting biomolecules, for example, such as proteins, genes and the like since almost all of organic molecules have specific Raman shifts ($cm^{-1}$) and are not affected by interference of water molecules. Since wavelengths of Raman emission spectrum provide chemical composition and structural properties of a light absorbed molecule, it can be used to directly analyze an analyte using the Raman signals. However, despite this availability, Raman spectroscopy has not been commercialized since a high-performance device is required to detect week signals of Raman spectroscopy.

Various methods have been developed to enhance the Raman signals. There are two primary mechanisms of enhancement, an electromagnetic and a chemical enhancement. The electromagnetic effect is dominant. The electromagnetic enhancement is dependent on the presence of the metal surface's roughness features. The surface-enhanced Raman signals are observed primarily for an analyte adsorbed onto the surface of a coinage metal, for example, such as Au, Ag, Cu or an alkali metal, for example, such as Li, Na, K, with the excitation wavelength near or in the visible region. The intensity of the Raman signal is proportional to the square of the magnitude of any electromagnetic field incident on an analyte and the electromagnetic field is sum of the electromagnetic field applied to the analyte in the absence of metal roughness features and the electromagnetic field resulted from the particulate metal roughness features. There are efforts to manufacture a substrate, which can provide surface-enhanced Raman signals significantly enhanced to a high level by controlling surface structure, particularly roughness, in various fields. Nat. Nanotechnology, 2010, 5(10): 732-736; Chin. Phys. Lett., 2007, 24(10): 2934-2937 reported significantly enhanced Raman signals on a structure including several nanometers of gaps. Accordingly, the inventor of this disclosure are to provide a substrate for surface-enhanced Raman spectroscopy which includes nanogaps uniformly distributed in a large scale. The substrate for surface-enhanced Raman spectroscopy is prepared by forming metal-containing nanoparticles on protuberant structures by depositing a metal, which is a Raman active material, on a polymer substrate through a vapor deposition and forming a metal-containing thin layer formed on a part or the entire part of the surface of the polymer substrate where the protuberant structures are not formed. Here, the size of the metal nanoparticles is controlled by controlling metal vapor deposition according to the distance between the protuberant structures to arrange the metal nanoparticles in constant intervals of several nanometers.

Throughout the description of the present disclosure, a term "surface Plasmon resonance (SPR)" is the collective oscillation of conduction electrons at the interface between a negative and positive permittivity material stimulated by incident light. The resonance condition is established when the frequency of incident photons matches the natural frequency of surface electrons oscillating against the restoring force of positive nuclei. Particularly, the surface Plasmon resonance resulting the confinement of a surface plasmon in a nanoparticle of size is called as a localized surface plasmon resonance. A material adsorbed on a metal surface, for example, such as Au or Ag, can be analyzed using the surface plasmon resonance.

A substrate for surface-enhanced Raman spectroscopy according to an example may include metal nanoparticles, particularly circular or oval metal nanoparticles, on protuberant structures of a polymer substrate, and a metal-containing thin layer formed on a part or the entire part of the surface of the polymer substrate where the protuberant structures are not formed. The substrate for surface-enhanced Raman spectroscopy may provide synergistic signal-enhanced effects to sensitively detect Raman signals due to the surface plasmon resonance between nanoparticles which are spaced several nanometers apart with each other on the protuberant structures, and the surface plasmon formed by the metal-containing thin layer formed on the part of the surface of the polymer substrate where the protuberant structures are not formed and formed a few tens of nanometers away from the nanoparticles. When a metal is deposited on the polymer substrate including protuberant structures through sputtering, the metal may be first deposited uniformly on the protuberant structures and the space between the protuberant structures. However, the metal may be intensively deposited on the protuberant structures as the deposition is progressed due to shadow effect caused by the sputtered particles. Because the surface, where the protuberant structures are not formed, may be blocked by adjacent protuberant structures and spherically growing nanoparticles on the structures, an amount of the metal which reaches to the surface may be significantly reduced.

When asymmetric accumulation of negative charges is caused on protuberant structures formed on the polymer substrate, it may induce concentration of positive ions or metal ions on protuberant structures. Therefore, the metal ions may be intensively deposited to form and grow nanoparticles on the protuberant structures where the negative charges are accumulated. This metal deposition on the protuberant structures of the polymer substrate may form not a continuous film but independent spherical nanoparticles. The metal particles may not be uniformly deposited on the protuberant structures due to negative charges selectively accumulated on the protuberant structures, poor bond between the polymer and the metal, and high curvature of a upper part of the protuberant structures. The metal particles may not be grown on the side surfaces of the structures due to poor bond between the polymer and the metal and low wettability.

The protuberant structures may be spaced-apart in constant intervals to provide the substrate having the structural features described above. For example, the protuberant structures may be spaced-apart in constant intervals of 10 to 500 nm, preferably in constant intervals of 20 to 200 nm, and more preferably in constant intervals of 40 to 80 nm. When the distance between the protuberant structures becomes less than 10 nm, the metal nanoparticles to be formed on the protuberant structures may not be formed as independent particles which are spaced-apart in a distance of several nanometers but may be formed as a continuous film. On the other hand, when the distance between the protuberant structures becomes greater than 500 nm, the metal-containing thin layer may be thickly formed since the portion where the shadow effect can be applied becomes broad. Therefore, the boundaries between the portion and nanoparticles formed on the protuberant structures may be blurred. The size of the nanoparticles may become bigger to maintain the gaps between nanoparticles in a nanometer level. The density of the nanogaps per unit area may be also reduced and the number of spots may be thus decreased to enhance Raman signals.

As described above, the protuberant structures may include the protruded curved surface. An etching method may be thus used rather than an imprinting method which provides flat and angled structures. The protuberant structure may be formed by dry etching the surface of the polymer substrate. The dry etching may be a plasma dry etching performed by using at least one gas chosen from argon, oxygen, hydrogen, helium and nitrogen gas. However, the method is not limited thereto and other method may be used departing from the spirit and scope of the illustrative examples described. The plasma dry etching of the polymer substrate may be carried by various methods known in the art. The plasma dry etching may be performed to the polymer substrate to form protrusions. Space and size of the protrusions may be controlled by changing various factors, for example, such as flow rate of the gas and power that forms plasma, exposure time to the plasma and the like.

The metal-containing nanoparticles and the metal-containing thin layer may be formed by a vapor deposition of the first surface of the polymer substrate on which protuberant structures having protruded curved surface are formed to be spaced-apart. The vapor deposition may be performed by sputtering, evaporation and chemical vapor deposition. However, it is not limited thereto.

The metal-containing nanoparticles on the protuberant structures may be formed in a spherical or oval shape. However, the shape of the metal-containing nanoparticle is not limited thereto. The metal-containing nanoparticles may have an average particle size of 5 nm to 1 μm. The metal-containing nanoparticles may have an average particle size of 10 nm to 300 nm. However, the size of metal-containing nanoparticles may not be limited thereto.

A horizontal maximum width W1 of the metal-containing nanoparticles which are formed vertically to the polymer substrate may equal to or greater than a horizontal maximum width W2 of the protuberant structure which is formed vertically to the polymer substrate, and less than the shortest distance W3 between centers of the protuberant structures. For example, when the horizontal maximum width W1 of the metal-containing nanoparticles is less than the horizontal maximum width W2 of the protuberant structure, enhancement of Raman effects may not be provided. When the size is less than that of the protuberant structure which does not show enhancement of Raman effects, efficient enhancement of Raman effect may not be provided since the distance between the nanoparticles increases. On the other hand, when the horizontal maximum width W1 of the metal-containing nanoparticles is greater than the shortest distance W3 between centers of the protuberant structures, nanogaps which provide significant enhancement of Raman signals may not be formed, but an embossed surface having unevenness of a continuous curved surface may be formed.

Since the structure with a gap of several nanometers provides significant enhancement of Raman signals, nanogaps of the surface-enhanced Raman spectroscopy may be formed in a range of 1 to 10 nm which may be controlled by the distance between the metal-containing nanoparticles. The distance between the metal-containing nanoparticles may be controlled by adjusting the distance between the protuberant structures and size of the metal-containing nanoparticles formed on the protuberant structures.

The metal-containing nanoparticles may be nanoparticles including a Raman active material, for example, such as a metal, a metal oxide and a metal nitride. The metal of the metal-containing nanoparticles may be chosen from Au, Ag, Cu, Pt and Pd, and an alloy thereof to enhance of Raman signals of an analyte adsorbed on the metal by providing the electromagnetic field enhance by the surface Plasmon resonance.

The polymer substrate may be formed of a polymer chosen from acrylic polymer, polyethersulfone (PES), polycycloolefin (PCO), polyiourethane and polycarbonate (PC) to provide uniformly arranged protuberant structures on the substrate through the plasma dry etching. The polymer substrate may be also formed by forming a reinforced coating layer including the polymer on another substrate. Preferably, the polymer substrate may be a substrate formed of an acrylic polymer itself or a substrate on which a reinforced coating layer including an acrylic polymer is formed. Examples of the acrylic polymer may be poly (methyl methacrylate) (PMMA), polymethacrylate, poly(methyl acrylate) (PMA), poly(ethyl acrylate) (PEA), poly(2-chloroethyl vinyl ether) (PCVE), poly(2-ethylhexyl acrylate) (PEHA), poly(hydroxyethyl methacrylate) (PHEMA), poly(butyl acrylate) (PBA), poly(butyl methacrylate) (PBMA), polyethylene terephthalate (PET), polyethylene naphthalate (PEN) and poly(trimethylolpropane triacrylate) (PTMPTA). However, the acrylic polymer is not limited thereto. The reinforced coating layer may include a polymer coating material chosen from an acrylic coating material, a poly urethane-based coating material, an epoxy-based coating material, and primer-based coating material. The reinforced coating layer may further include inorganic fine particles chosen from a metal oxide, a metal sulfide, alumina, silica, a zirconium oxide and an iron oxide. The reinforced coating layer may be formed in a thickness of 1 to 10 m on a substrate.

A method for producing a substrate for surface-enhanced Raman spectroscopy may include forming protuberant structures having protruded curved surface to be spaced-apart by dry etching a first surface of a polymer substrate; and forming metal-containing nanoparticles on the protruded curved surfaces of the protuberant structures and a metal-containing thin layer on a part or the entire part of the first surface of the polymer substrate where the protuberant structures are not formed at the same time by a vapor deposition with a metal-containing Raman active material till nanogaps are formed between the metal-containing nanoparticles adjacent with each other.

The vapor deposition may be performed by sputtering, evaporation and chemical vapor deposition.

The method for producing a substrate for surface-enhanced Raman spectroscopy can produce a substrate for surface-enhanced Raman spectroscopy at a large scale with simple equipment and at a low production cost. The substrate manufactured thereby may allow quantitative analysis due to reproducible enhancement effect. The large scale may be 1 $mm^2$ to 10 $m^2$, preferably 1 $mm^2$ to 1000 $cm^2$. However, the scale is not limited thereto. An area of the substrate manufactured by the method described herein may vary with the etching method which provides uniformly spaced-apart protuberant structures and the sputtering method which provides uniformly sputtered metal-containing Raman active material. Thus, the area of the substrate may increase as the etching method and the sputtering method are more developed.

The substrate manufactured by the method described herein may allow notably improved surface-enhanced Raman signals, even in cases of long-term storage, for example, such as several tens of days due to excellent durability. Since the substrate includes metal-containing particles which are distanced several nanometers apart, it may not be easy to cause an oxidation reaction between those narrow spaces even though the substrate is exposed into the atmosphere. When a surface is treated with a metal as a conventional Raman active material, the metal becomes oxidized and Raman signals are thus significantly decreased as the exposure time into the atmosphere increases. However, the substrate according to an example may still maintain the improved Raman signals at a high level.

Figure 6:
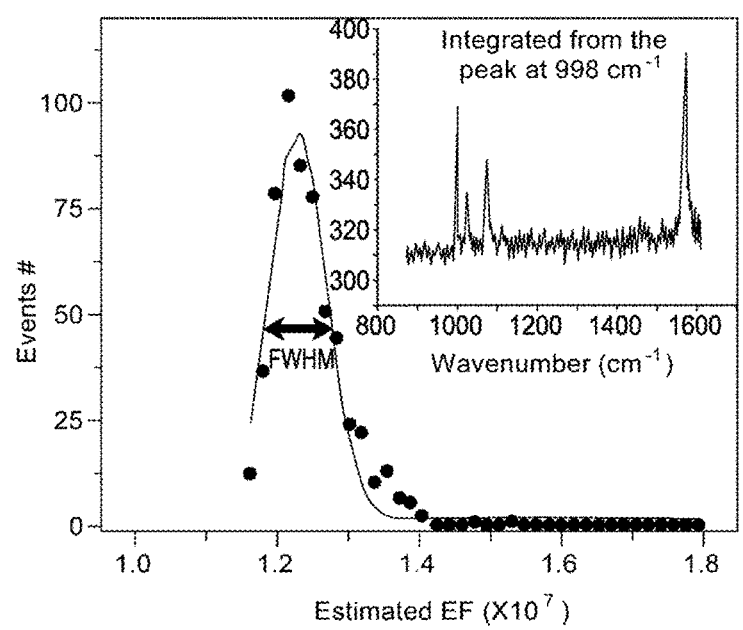
FIG. 6 is a distribution graph illustrating estimated EF values at each pixel based on a Raman mapping using an example of a substrate for surface-enhanced Raman spectroscopy.
Figure 7:
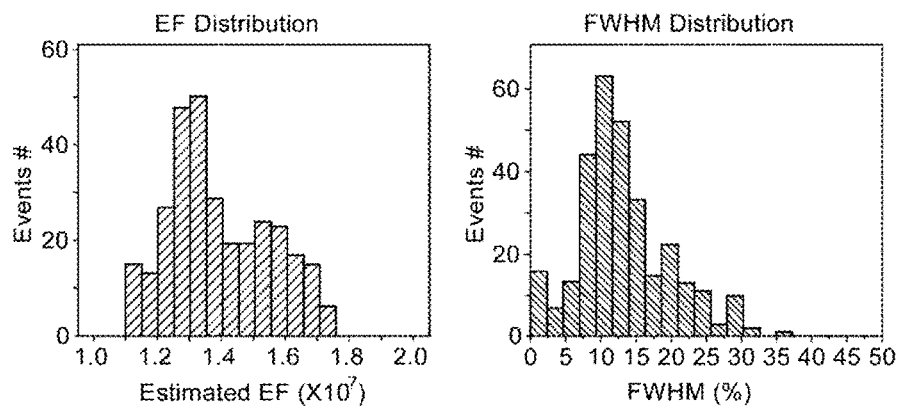
FIG. 7 is a graph illustrating uniformly enhanced Raman signal at a large scale of an example of a substrate for surface-enhanced Raman spectroscopy. FW-HM distributions and center values of each experiment obtained by Gaussian fitting of the EF distributions which are estimated for an area of 10 μm×10 μm after performing more than 300 times are plotted.

It is noted in FIG. 6 that the substrate according to an example shows improved Raman signals at a very constant level in a Raman map with 32 pixel×32 pixel resolution for an area of 10 μm×10 μm. It is also noted in FIG. 7 that the reproducibility is within a deviation of about 6% after the same experiment is repeated more than 300 times. It is further noted in FIG. 8 that when the substrate is stored for more than 40 days, the improved Raman signals are sustained at the same level, compared to the level when the immediately prepared substrate shows.

A Raman spectroscopic device according to an example may include a light source; the substrate for surface-enhanced Raman spectroscopy described above; and a detector configured to detect Raman spectrum.

The Raman effects of Raman spectroscopy is very week. Thus, a Raman spectroscopic device equipped with the substrate for surface-enhanced Raman spectroscopy according to an example may be provided in order to resolve this problem. The light source may be a laser which can provide high dense photons. The detector may include a photomultiplier tube (PMT), an avalanche photodiode (APD), a charge coupled device (CCD) and the like to efficiently amplify signals.

A method for detecting Raman spectroscopy of an analyte according to an example may include: preparing the substrate for surface-enhanced Raman spectroscopy described above; approaching or contacting an analyte to the substrate; irradiating the analyte; and detecting scattered Raman signals of the analyte.

The substrate for surface-enhanced Raman spectroscopy including metal nanoparticles which are spaced several nanometers apart on a substrate can be manufactured at a large scale with simple equipment and at a low production cost. Additionally, as the distance between the metal nanoparticles can be reproducibly produced to be several nanometers, the Raman signals can be notably improved, and even in the case of long-term storage, the improved Raman signals can be sustained at a high level.

Other features and aspects will be apparent from the following detailed description, the drawings, and the claims.

EXAMPLE 1

Preparation of a Substrate for Surface-Enhanced Raman Spectroscopy Including Nanogaps and Property Analysis Step 1: Forming Protuberant Structures by Plasma Dry Etching A dry etching was performed on a polymer substrate formed of polyethylene terephthalate having a thickness of 188 μm which was purchased from Panac Co. using a 13.56 MHz capacitively coupled plasma-typed power supply. An etching system was composed of a shower head part with a diameter of 6 in. including an annular stainless steel tube with a diameter of 0.23 in. and an electrode with a diameter of 6 in. formed on the upper part which is 15 cm apart from the shower head part.

Figure 3:
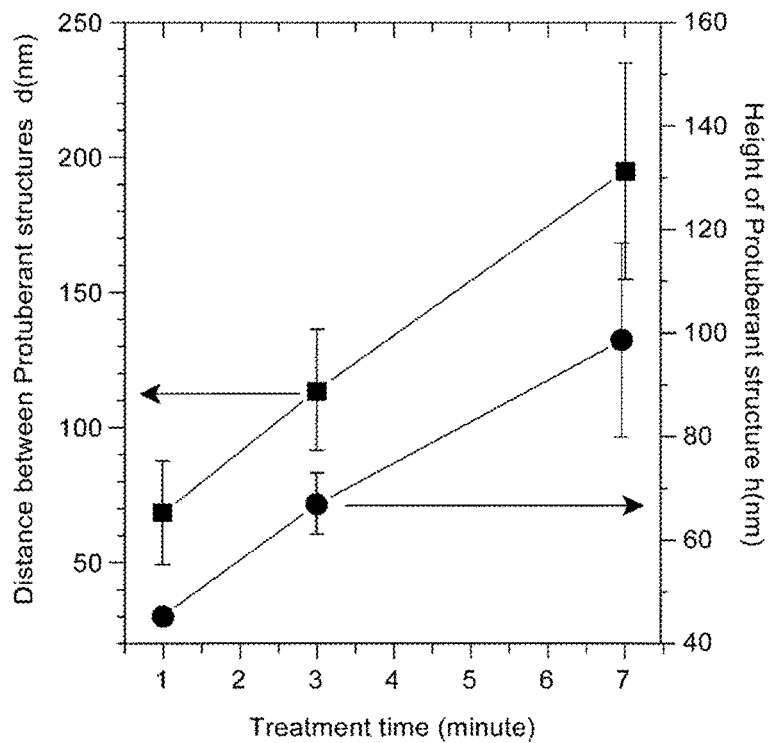
FIG. 3 is a graph illustrating height of and distance between protuberant structures on an example of a substrate depending on plasma treatment time.

In particular, the polymer substrate with a thickness of 125 μm purchased from Panac Co. was attached to the electrode. A 99.999% Argon gas was supplied to a reactor through the shower head at a flow rate of 50 sccm to increase a pressure of a reaction chamber to 22.7 Pa when the pressure of the reaction chamber was reached to a vacuum level of 6.7 Pa. The plasma dry etching was performed at a RF power of 200 W which is 1.1 W/cm² by changing etching time. A plasma ion energy applied from self-bias to the polymer substrate was 102 eV during the etching process. A temperature of the polymer substrate was kept at 50° C. or lower during the etching process. A distance of nanometer scale between protuberant structures formed on the polymer substrate was linearly increased as the etching time increases. When the etching was processed for 1 min or less under this condition, the distance between protuberant structures was in a range of 40 to 80 nm (see FIG. 3). The distance between and the size of the protuberant structure were determined using AFM cross-section profile.

Step 2: Deposition of a Metal-Containing Raman Active Material

Ag particles of a Raman active material were deposited on the surface including the protuberant structures of the polymer substrate prepared in Step 1 using a sputtering vapor deposition method. The deposition was performed using a magnetron multi-gun sputtering system (A-Tech System Co., Ltd., Flexlab system 100) at room temperature.

In particular, the polymer substrate, on which the protuberant structures were formed using the plasma dry etching method in Step 1, was mounted at a substrate holder which is positioned at the upper 15 cm of an Ag sputtering target in the sputtering system. After a pressure of a deposition chamber was reduced to $4.5 \times 10^{-6}$ Torr, 99.999% Argon gas was supplied at a flow rate of 45 sccm to increase the pressure to 3 mTorr. Ag particles were deposited by DC reactive sputtering using Ag target with a diameter of 4 in. (Williams Advanced Materials Inc.) and a DC power of 0.13 W/cm². Ar plasma pretreatment was performed on the polymer protuberant structures for 60 seconds under RF 200 W to form Ag nanoparticles with a size of 60 nm and a thin film on the substrate on which the protuberant structures are not formed by sputtering.

As a result, circular or oval Ag nanoparticles were formed on the protuberant structures of the polymer substrate and the thin film was formed on the substrate on which the protuberant structures are not formed.

A substrate for surface-enhanced Raman spectroscopy was prepared by forming protuberant structures on a polymer, for example, such as PC, PEN and PET substrates and then depositing Ag nanoparticles as described above.

Figure 4:
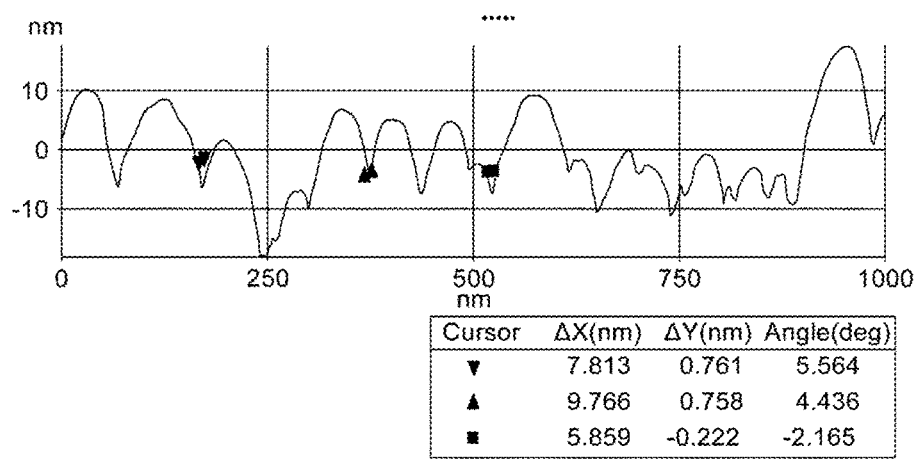
FIG. 4 is a graph illustrating a depth profile of an Atomic Force Microscopic image and a sectioned surface for the surface of an example of a substrate for surface-enhanced Raman spectroscopy.

The polymer surface on which the Ag nanoparticles are formed was scanned using an Atomic Force Microscope to determine distance between the Ag nanoparticles and height between the top part of the Ag nanoparticles and the substrate surface on which the Ag thin film is formed but the protuberant structures are not formed. FIG. 4 is a graph illustrating the distance and the height. The Ag nanoparticles formed on the protuberant structures have gaps of several nanometers between each other. Moreover, the average height between the top part of the Ag nanoparticles and the substrate surface on which the Ag thin film is formed but the protuberant structures are not formed is about 10 nm to provide additional enhanced Raman signals.

Optimizing Raman signal enhancement by controlling the distance between the nanoparticles can be achieved by not only controlling time and conditions of the plasma dry etching in Step 1 to control size and distance of the protuberant structures but also controlling time and conditions of the sputtering in Step 2 to control size of the nanoparticles.

EXAMPLE 2

Optical Properties of the Substrate for Surface-Enhanced Raman Spectroscopy

Figure 5:
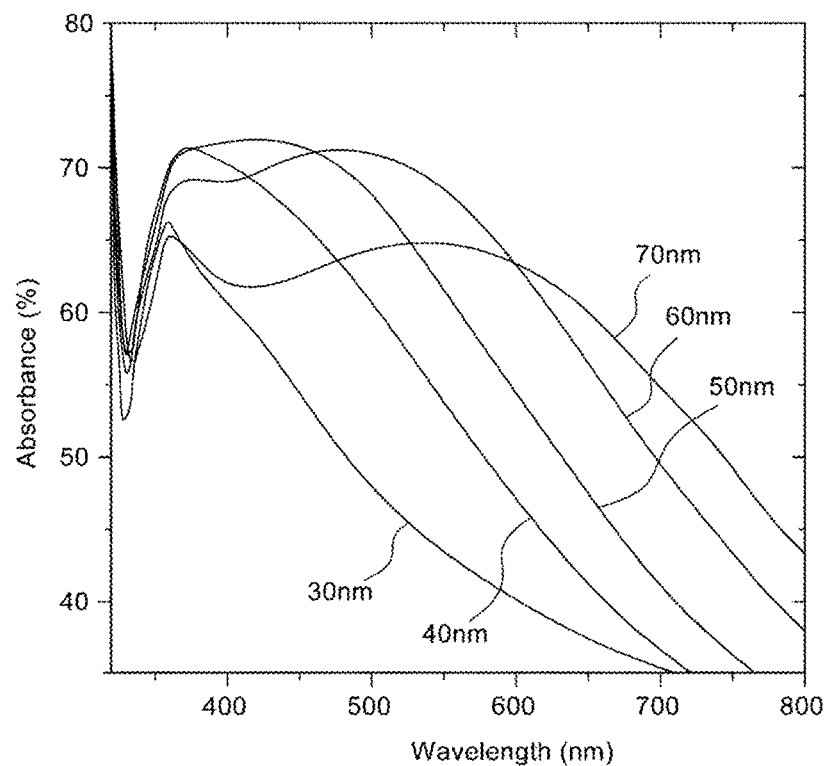
FIG. 5 is a graph illustrating absorbance according to size of metal nanoparticles formed on protuberant structures on a polymer substrate by a vapor deposition.

Optical properties of the substrate for surface-enhanced Raman spectroscopy including the metal nanoparticles on the PET polymer substrate prepared in Example 1 were determined. The distance between metal nanoparticles of the substrate for surface-enhanced Raman spectroscopy was controlled to be in a range of several nanometers by controlling the distance between the protuberant structures in Step 1 and the size of the metal nanoparticles in Step 2. As shown in FIG. 5, the metal nanoparticles showed high absorbance at a specific wavelength region for an incident light. A position of the maximum absorption wavelength was changed depending on size of the nanoparticles. The optical properties contribute to properties of the surface-enhanced Raman spectroscopy.

EXAMPLE 3

Detection of Raman Signals from the Substrate for Surface-Enhanced Raman Spectroscopy Enhancement effect of the substrate for surface-enhanced Raman spectroscopy prepared in Example 1 was determined on Raman signals of an analyte using benzenethiol as a sample. 2 M benzenethiol solution 100 μl was dropped on 2.5 cm×1.3 cm size of the substrate for surface-enhanced Raman spectroscopy and dried for 1 hour. The substrate for surface-enhanced Raman spectroscopy on which benzenethiol was adsorbed was rinsed with ethanol several times and dried with $N_2$. Raman signals of an analyte was determined at a 10 μm×10 μm region of the substrate for surface-enhanced Raman spectroscopy on which the analyte was adsorbed. A 532 nm wavelength laser of 0.2 mW was used to irradiate. A 10 μm×10 μm area was divided into 32 pixel×32 pixel for a point to obtain a spectrum to be a diffraction limit and exposed for 2 seconds to provide Raman spectrum. An enhancement factor (EF) was provided by converting a peak area shown at the 998 $cm^{-1}$ region of benzenethiol for Raman mapping. EF values were mapped in the 10 μm×10 μm region. A part thereof was enlarged and EF values determined at each pixel was shown in FIG. 6.

As shown in FIG. 6, Raman signals were determined at the 10 μm×10 μm region, total 32×32 which is 1024 pixels and the EF values converted therefrom were distributed in a 1.1 to $1.4 \times 10^7$ region. It was shown normal distribution (Gaussian) with narrow FWHM (full-width half maximum) of about $0.1 \times 10^7$ which showed maximum distribution at about $1.25 \times 10^7$ and also relatively even EF values at a large area. It is noted that when the substrate for surface-enhanced Raman spectroscopy according to an example is used, signal enhancement effects are exhibited in a large area so that it can be suitable for both qualitative analysis and quantitative analysis.

Raman mapping experiments were performed more than 350 times to determine reproducibility of Raman signals using the substrate for surface-enhanced Raman spectroscopy according to an example and statistical EF values were determined. Those EF values were distributed in a similar region to the 1.1 to $1.7 \times 10^7$ region where EF values were distributed in the single mapping and showed maximum distribution at about $1.3 \times 10^7$. FWHM distribution was obtained from each mapping. It is noted that the FWHM from each mapping shows 0 to 25% to the average value obtained from the single mapping and the maximum distribution shows 10 to 15% to the average value obtained from the single mapping. The reproducibility experiments were performed using samples prepared from 5 batches to show that signal enhancement can be reproducibly provided in the substrates produced by same manufacturing process.

It is clearly shown that the substrate for surface-enhanced Raman spectroscopy according to an example uniformly enhances Raman signals over a large area and allows reproducible enhancement even after repeating hundreds of times. Thus, it can be suitable for both qualitative analysis and quantitative analysis.

EXAMPLE 4

Stability of the Substrate for Surface-Enhanced Raman Spectroscopy

A stability test on exposure to air was performed to commercialize the substrate for surface-enhanced Raman spectroscopy according to an example. Statistical EF values were provided after Raman mapping more than 350 times at each point and then plotted as a function of storage time. The substrate was exposed to the air with a temperature of 22° C. and a humidity of 40%. The result is shown in FIG. 8.

Figure 8:
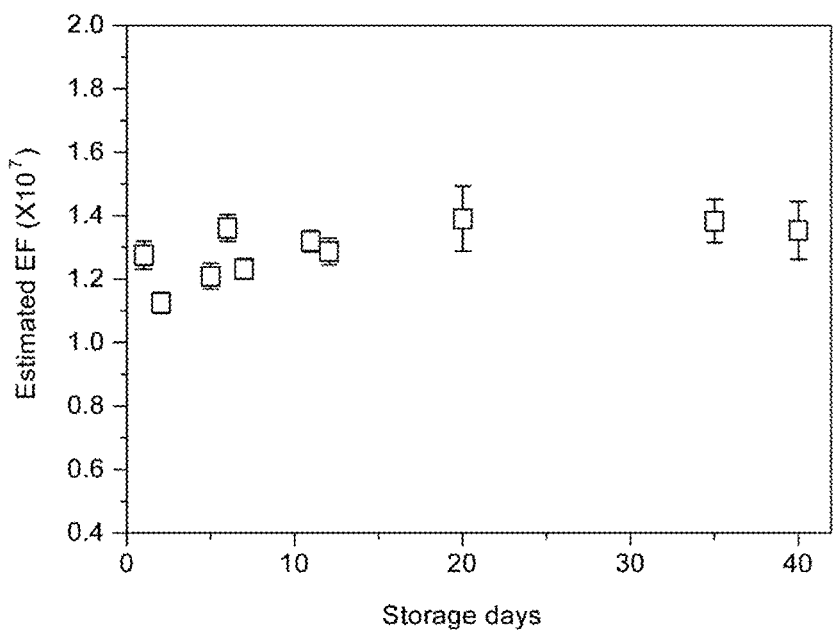
FIG. 8 is a diagram illustrating stability of an example of a substrate for surface-enhanced Raman spectroscopy after exposed to air. Statistical EF values are obtained by performing Raman mappings more than 350 times at each point and the result is shown as a function of storage time. The substrate is exposed to air with temperature of 22° C. and humidity of 40%.

As shown in FIG. 8, when the substrate for surface-enhanced Raman spectroscopy was exposed to the atmosphere for more than 40 days, it showed enhanced effect (EF=1.1 to $1.4 \times 10^7$) which was similar to the level shown when it was used immediately after being prepared.

This proposes a key solution in commercialization of the substrate for surface-enhanced Raman spectroscopy since it resolves the drawback of the conventional substrates for surface-enhanced Raman spectroscopy of which surfaces including metal nanostructures are oxidized due to exposure to the atmosphere as time passes.

The substrate for surface-enhanced Raman spectroscopy, which is prepared by vapor depositing a Raman active metal on the polymer substrate, on which the protuberant structures are uniformly formed, to arrange nanoparticles to have nanogaps by controlling the size of and the distance between the nanoparticles on protuberant structures, can be manufactured at a large scale with simple equipment and at a low production cost since the manufacturing method is simple and does not require cost equipments. The substrate for surface-enhanced Raman spectroscopy can be uniformly formed at large scale production to be suitable for mass production. Additionally, as the distance between the metal nanoparticles can be reproducibly produced to be several nanometers, the Raman signals can be notably improved, and even in the case of long-term storage, the improved Raman signals can be sustained at a high level. It can be thus suitable for both qualitative analysis and quantitative analysis and can be commercialized.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A substrate for surface-enhanced Raman spectroscopy comprising:
    a polymer substrate of which protuberant structures having an upper protruded curved surface are formed to be spaced-apart on a first surface;
    metal-containing nanoparticles formed on the protuberant structures; and
    a metal-containing thin layer formed on a part or the entire part of the first surface of the polymer substrate where the protuberant structures are not formed,
    wherein the metal-containing nanoparticles and the metal-containing thin layer are formed by a vapor deposition with a metal-containing Raman active material on the first surface at the same time, and
    wherein the metal-containing Raman active material is first deposited uniformly on the first surface and on the protuberant structures but intensively on the protuberant structures as the deposition is progressed.

2. The substrate of claim 1, wherein the protuberant structures are equally spaced-apart.

3. The substrate of claim 2, wherein the protuberant structures are spaced-apart in intervals of 10 to 500 nm.

4. The substrate of claim 1, wherein the protuberant structure is formed by dry etching the surface of the polymer substrate.

5. The substrate of claim 1, wherein the vapor deposition is performed by sputtering, evaporation or chemical vapor deposition.

6. The substrate of claim 1, wherein the metal-containing nanoparticles on the protuberant structures are formed in a spherical or oval shape.

7. The substrate of claim 1, wherein the metal-containing nanoparticles have an average particle size of 5 nm to 1 µm.

8. The substrate of claim 7, wherein the metal-containing nanoparticles have an average particle size of 10 nm to 300 nm.

9. The substrate of claim 1, wherein a horizontal maximum width W1 of the metal-containing nanoparticles which are formed vertically to the polymer substrate is equal to or greater than a horizontal maximum width W2 of the protuberant structures which are formed vertically to the polymer substrate, and less than the shortest distance W3 between centers of the protuberant structures.

10. The substrate of claim 1, wherein the space interval between the metal-containing nanoparticles is controlled by controlling a distance between the protuberant structures and a size of the metal-containing nanoparticle formed on the protuberant structure.

11. The substrate of claim 1, wherein the metal-containing nanoparticle forms a nanogap with an adjacent metal-containing nanoparticle, an adjacent metal-containing thin layer or both, and the nanogap is formed in a range of 1 to 10 nm.

12. The substrate of claim 1, wherein the metal-containing nanoparticle is a metal, a metal oxide or a metal nitride.

13. The substrate of claim 1, wherein a metal in the metal-containing nanoparticles is selected from the group consisting of Au, Ag, Cu, Pt and Pd, and an alloy thereof.

14. The substrate of claim 1, wherein the polymer substrate is formed of a polymer selected from the group consisting of acrylic polymer, polyethersulfone (PES), polycycloolefin (PCO), polyourethane and polycarbonate (PC), or the polymer substrate is formed by forming a reinforced coating layer comprising the polymer on another substrate, wherein the acrylic polymer is selected from the group consisting of poly(methyl methacrylate) (PMMA), polymethacrylate, poly(methyl acrylate) (PMA), poly(ethyl acrylate) (PEA), poly(2-chloroethyl vinyl ether) (PCVE), poly(2-ethylhexyl acrylate) (PEHA), poly(hydroxyethyl methacrylate) (PHEMA), poly(butyl acrylate) (PBA), poly(butyl methacrylate) (PBMA), poly(ethylene terephthalate) (PET), poly(ethylene naphthalate) (PEN) and poly(trimethylolpropane triacrylate) (PTMPTA).

15. The substrate of claim 14, wherein the reinforced coating layer comprises a polymer coating material chosen from an acrylic coating material, a poly urethane-based coating material, an epoxy-based coating material, and primer-based coating material.

16. The substrate of claim 14, wherein the reinforced coating layer further comprises inorganic fine particles selected from the group consisting of a metal oxide, a metal sulfide, alumina, silica, a zirconium oxide and an iron oxide.

17. The substrate of claim 14, wherein the reinforced coating layer is coated in a thickness of 1 to 10 m.

18. A Raman spectroscopic device comprising a light source; a substrate for surface-enhanced Raman spectroscopy of claim 1; and a detector configured to detect Raman spectrum.

19. A method for detecting Raman spectroscopy of an analyte comprising:
    providing a substrate for surface-enhanced Raman spectroscopy of claim 1;
    approaching or contacting an analyte to the substrate;
    irradiating the analyte; and
    detecting scattered Raman signals of the analyte.

20. A method for producing a substrate for surface-enhanced Raman spectroscopy, the method comprising:
    forming protuberant structures having an upper protruded curved surface to be spaced-apart by dry etching a first surface of a polymer substrate; and
    forming metal-containing nanoparticles on the protruded curved surfaces of the protuberant structures and a metal-containing thin layer on a part or the entire part of the first surface of the polymer substrate where the protuberant structures are not formed at the same time by a vapor deposition with a metal-containing Raman active material till nanogaps are formed between the metal-containing nanoparticles adjacent with each other,
    wherein the metal-containing Raman active material is first deposited uniformly on the first surface and on the protuberant structures but intensively on the protuberant structures as the deposition is progressed.

* * * * *